United States Patent [19]

May

[11] 3,982,278
[45] Sept. 28, 1976

[54] ALIGNMENT DEVICE FOR ARTIFICIAL LIMBS

[75] Inventor: Denis Ronald William May, London, England

[73] Assignee: J. E. Hanger & Company Limited, London, England

[22] Filed: Jan. 29, 1976

[21] Appl. No.: 653,605

[30] Foreign Application Priority Data

Feb. 21, 1975 United Kingdom................ 7288/75

[52] U.S. Cl............................................. 3/21; 3/30
[51] Int. Cl.²........................ A61F 1/08; A61F 1/04
[58] Field of Search............ 3/21, 2, 6, 7, 12, 30–35

[56] References Cited
UNITED STATES PATENTS

| | | | |
|---|---|---|---|
| 3,538,516 | 11/1970 | Bailey et al. | 3/21 |
| 3,551,915 | 1/1971 | Woodall | 3/21 |
| 3,659,294 | 5/1972 | Glabiszewski | 3/21 |

FOREIGN PATENTS OR APPLICATIONS

| | | | |
|---|---|---|---|
| 2,217,261 | 3/1973 | Germany | 3/21 |

*Primary Examiner*—Ronald L. Frinks
*Attorney, Agent, or Firm*—Imirie, Smiley & Linn

[57] ABSTRACT

The invention provides an alignment device for use between a tube socket and a weight-bearing element of an artificial limb in which a desired angular relationship set by jacking screws and maintained by a controlled degree of friction between concentric part-spherical surfaces is maintainable despite the unlocking of clamping screws applying force between the said surfaces.

5 Claims, 3 Drawing Figures

U.S. Patent  Sept. 28, 1976  3,982,278
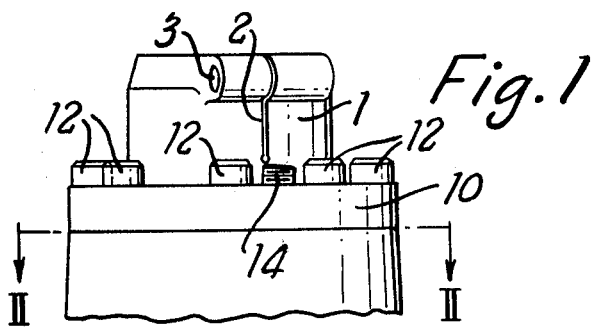
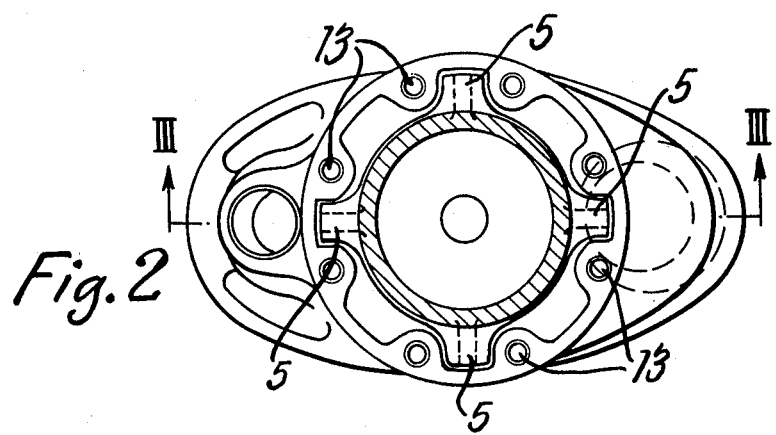
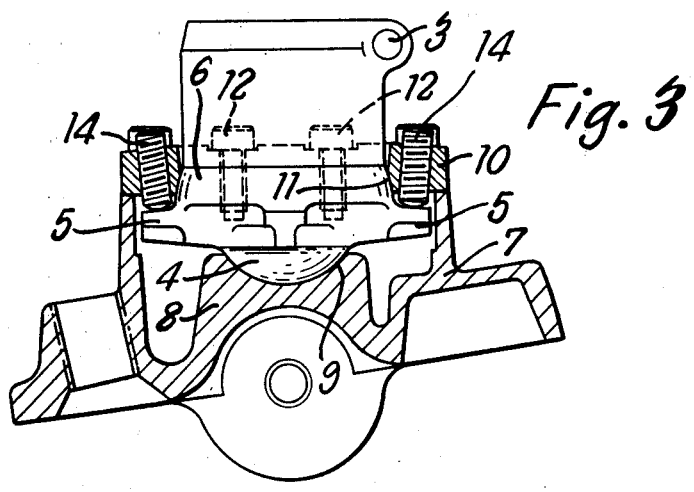

ALIGNMENT DEVICE FOR ARTIFICIAL LIMBS

This invention concerns an improved alignment device for artificial limbs of the kind intended to maintain a desired angular relationship between two structural elements. More particularly it is concerned with the adjustably aligned inter-connection of a tube socket and the cast housing of a limb element, such as an ankle joint.

Conventional alignment devices are so designed that when locking means are loosened complete freedom of angular and rotary motion is permitted so that a previous setting cannot be regained.

The present invention aims to provide a device which can be slackened or even completely dismantled without loss of a desired alignment setting.

According to the invention we provide an alignment device for a tube socket and an artificial limb element comprising two oppositely facing concentric part-spherical convex surfaces formed on the end of the socket which are engaged by complementary concave surfaces formed within the limb element and within a clamping ring, clamping screws passing through plain holes in the ring into threaded holes in the limb element, tightening of which can induce a controlled degree of frictional resistance between the said part-spherical surfaces, and at least one pair of jacking screws passing through threaded holes in the ring on at least one diameter thereof to engage abutments on the socket, the arrangement being such that an angular alignment between the socket and the limb element set by operation of the jacking screws can be maintained by pure friction between the part spherical surfaces.

When the device is used as alignment means between a shin tube and the ankle joint of an artificial foot, only one pair of jacking screws may be employed in the locking ring and be arranged on a diameter parallel to the ankle pivot axis, thus permitting deliberate change of alignment in the fore and aft direction on the application of force sufficient to overcome predetermined frictional resistance of the engaged part-spherical surfaces.

This is an important facility of the device since a patient requires a different attitude of the foot relative to the shin for comfort in walking up or down a slope, and ladies in particular requires a different foot attitude in accordance with the height of their shoe heels.

The actual frictional resistance to movement in the alignment device is dependent upon the degree of tightening of the clamp ring screws and may be set with the use of a torque measuring tool. It must be high enough to permit normal functioning of ankle joint means without disturbance of foot attitude, but sufficiently low as permit deliberate attitude shifting by application of the patient's weight.

Preferably the tube socket is a steel investment casting and is unpolished to give the concentric part spherical surfaces thereon a high friction characteristic.

The limb element forming part of the device will normally be a light alloy casting, and will include at least one pivot bearing for a load-bearing structure.

The above and other features of the invention are embodied in one constructional form of alignment device, which will now be described by way of example with reference to the accompanying informal drawings, in which:-

FIG. 1 is a side elevation;
FIG. 2 is a section on the line II—II of FIG. 1; and
FIG. 3 is a section on the line III—III of FIG. 2.

In the drawings, FIG. 1 shows a tube socket 1 with an axial slot 2 in its wall, for reception and retention of a tubular artificial limb member (not shown) upon tightening of a clamp screw (not shown) into a threaded hole 3.

The tube socket 1 is a steel investment casting which is formed at its base with a part-spherical protrusion 4, four radially extending lugs 5 and a part-spherical shoulder 6 concentric with the protrusion 4 (FIGS. 2 and 3).

A limb element in the form of a light alloy casting 7 constituting part of an ankle joint includes a central boss 8 having a concave part-spherical surface 9 complementary to the surface of the protrusion 4.

A clamp ring 10 is fitted over the shoulder 6 and has a concave part-spherical surface 11 complementary to the surface of that shoulder. It is urged towards the casting 7 by eight regularly spaced screws 12 which pass through plain holes 13 in ring 10.

Four jacking screws 14 fitted in threaded holes in the clamp ring abut the lugs 5 of the tube socket 1 to adjust the angular relationship between socket and casting.

The eight clamping screws are capable of applying such a large force to the shoulder 6 and the complementary surfaces of the protrusion 4 and casting boss 8 that high friction prevents angular movement of the socket relative to the casting except through the agency of the jacking screws.

However, as explained previously, the degree of frictional resistance to movement may be adjusted to a predetermined maximum by only partially tightening the clamping screws, in which case the omission of the pair of jacking screws 14 shown in FIG. 3 will permit a limited degree of rocking movement on application of sufficient force.

It is a feature of the device that, once a desired alignment has been set by use of the jacking screws and they are left in adjusted position, the whole assembly may be taken apart and re-assembled without losing the desired alignment.

It will be understood that the invention is not restricted to the details of the preferred form described by way of example which may be modified without departure from the broad ideas underlying them.

I claim:

1. An alignment device for a tube socket and an artificial limb element comprising two oppositely facing concentric part-spherical convex surfaces formed on the end of the socket which are engaged by complementary concave surfaces formed within the limb element and within a clamping ring, clamping screws passing through plain holes in the ring into threaded holes in the limb element, tightening of which can induce a controlled degree of frictional resistance between the said part-spherical surfaces, and at least one pair of jacking screws passing through threaded holes in the ring on at least one diameter thereof to engage abutments on the socket, the arrangement being such that an angular alignment between the socket and the limb element set by operation of the jacking screws can be maintained by pure friction between the part spherical surfaces.

2. An alignment device according to claim 1 in which the socket is an unpolished steel investment casting.

3. An alignment device according to claim 1 in which the limb element comprises a light alloy casting including at least one pivot bearing for load-bearing structure.

4. An alignment device according to claim 1 in which the limb element is the ankle joint of an artificial foot.

5. An alignment device according to claim 4, in which jacking screws are provided only on a diameter of the clamping ring which is parallel to the pivot axis of the ankle joint.

* * * * *